United States Patent [19]

Biswas

[11] Patent Number: 4,750,806
[45] Date of Patent: Jun. 14, 1988

[54] GLASS FIBERS AND CAPILLARIES WITH HIGH TEMPERATURE RESISTANT COATINGS

[75] Inventor: Dipak R. Biswas, Roanoke, Va.

[73] Assignee: Alcatel USA Corporation, New York, N.Y.

[21] Appl. No.: 745,046

[22] Filed: Jun. 17, 1985

Related U.S. Application Data

[60] Continuation-in-part of Ser. No. 838,223, Mar. 10, 1986, abandoned, which is a division of Ser. No. 644,305, Aug. 24, 1984, Pat. No. 4,575,463, which is a continuation-in-part of Ser. No. 580,280, Feb. 17, 1984, Pat. No. 4,518,628, which is a continuation of Ser. No. 382,856, May 28, 1982, abandoned.

[51] Int. Cl.$^4$ .............................................. G02B 6/16
[52] U.S. Cl. ............................... 350/96.30; 350/96.32; 350/96.34; 427/163; 428/388
[58] Field of Search ............... 350/96.30, 96.31, 96.32, 350/96.33, 96.34; 428/379, 388, 389; 427/55, 163; 65/3.11, 3.12

[56] References Cited

U.S. PATENT DOCUMENTS

| | | | |
|---|---|---|---|
| 3,436,141 | 4/1969 | Comte | 350/96.32 |
| 4,028,080 | 6/1977 | Di Vita et al. | 350/96.30 X |
| 4,418,984 | 12/1983 | Wysocki et al. | 350/96.33 |
| 4,468,294 | 8/1984 | Hocker et al. | 204/27 |
| 4,512,629 | 4/1985 | Hanson et al. | 350/96.30 |
| 4,518,628 | 5/1985 | Biswas et al. | 427/55 |
| 4,575,463 | 3/1986 | Biswas et al. | 427/163 |
| 4,592,932 | 6/1986 | Biswas et al. | 427/163 |

FOREIGN PATENT DOCUMENTS

| | | | |
|---|---|---|---|
| 56-12602 | 2/1981 | Japan | 350/96.30 |
| 58-58501 | 4/1983 | Japan | 350/96.29 |
| 58-58502 | 4/1983 | Japan | 350/96.29 |
| WO82/01543 | 5/1982 | PCT Int'l Appl. | 350/96.33 |

OTHER PUBLICATIONS

Almeida et al., "On Line-Metal Coating of Optical Fibers", Optik, vol. 53, No. 3, Jun. 1979, pp. 231–233.

Hartman et al., "Fabrication and Testing of A Nickel-Coated . . . ", Electronics Letters, vol. 18, No. 5, Mar. 1982, pp. 224–226.

Beales et al., "Practical Barrier To Hydrogen Diffusion . . . ", Electronics Letters, vol. 20, No. 4, Feb. 1984, pp. 159–161.

Rand, M. J. et al., "Silicon Oxynitride Films on Fused Silica for Optical Waveguides," Applied Optics, vol. 11, No. 11, 11–1972, pp. 2482–2488.

Grand, G. et al., "Optical Polarisers of High Extinction Ratio Integrated on Oxidised Silicon Substrate," Electronics Letters, vol. 20, No. 18, 8–84, pp 730–731.

Primary Examiner—John Lee
Attorney, Agent, or Firm—Peter C. Van Der Sluys

[57] ABSTRACT

Solid fibers or capillaries are coated with a metal, alloy or dielectric capable of withstanding temperatures in excess of 300° C. and preferably 500° C. The coating is deposited by a heterogeneous nucleation thermochemical deposition process occurring on the surface of the fiber.

10 Claims, 1 Drawing Sheet

GLASS FIBERS AND CAPILLARIES WITH HIGH TEMPERATURE RESISTANT COATINGS

CROSS REFERENCE TO RELATED APPLICATIONS

This application is a continuation-in-part of U.S. application Ser. No. 838,223, filed Mar. 10, 1986, now abandoned which application is a division of U.S. application Ser. No. 644,305, filed Aug. 24, 1984, now U.S. Pat. No. 4,575,463, which application is a continuation-in-part of U.S. application Ser. No. 580,280, filed Feb. 17, 1984, now U.S. Pat. No. 4,518,628 which application is a continuation of U.S. application Ser. No. 382,856, filed May 28, 1982, now abandoned.

BACKGROUND OF THE INVENTION

This invention relates generally to glass fibers and, more particularly, to solid optical fibers and glass capillaries coated with high temperature, high strength materials.

Glass fibers are more routinely used for a variety of applications. For example, in fiber optics, glass optical fibers are used to transmit voice, information or data signals in the form of light. These optical fibers include a silica core surrounded by a silica cladding having a lower index of refraction and typically have a diameter of about 125 microns, although somewhat larger and somewhat smaller diameter fibers have also been utilized. These fibers are usually coated with polymeric materials to protect the glass surface from abrasion and to facilitate their handling. These polymeric materials cannot withstand continuous exposure to temperatures in excess of from about 200° C. to about 300° C. In those applications requiring exposure to higher temperatures, the fibers have been coated with metal by a dip coating process. See U.S. Pat. No. 4,432,606, issued Feb. 2, 1984. The metal coating has been applied by a dip coating process and is satisfactory for applications wherein the coated fiber is exposed to temperatures of up to about 500° C.

Glass capillaries are used in gas chromatography. These capillaries too are of a relatively small diameter and in the application noted above must withstand corrosive environments and temperatures in excess of 300° C. In addition, the capillaries must have high strength—they must be able to be wrapped on a drum of finite diameter without breaking. One type of small diameter capillary is drawn from a large diameter tube to reduce its cross-section and the reduced cross-section capillary is coated with a polymeric material to increase its strength and facilitate its being wrapped on a drum. Similar to the polymer coated optical fibers noted above, the resultant capillaries cannot withstand continuous exposure to temperatures in excess of about 300° C. Thus, their utility is limited.

SUMMARY OF THE INVENTION

It is an object of this invention to provide a glass fiber and a capillary that exhibits relatively high strength and which can withstand continuous exposure to relatively high temperatures, e.g., in excess of at least 300° C. and, preferably, in excess of 500° C.

This is accomplished by providing a glass fiber or capillary coated on its outer surface with a single coating selected from a group consisting of metal, metal alloy or dielectric material deposited by a heterogeneous nucleation thermochemical deposition (HNTD) process as described in U.S. Pat. No. 4,518,628 issued May 21, 1985.

BRIEF DESCRIPTION OF THE DRAWING

For a better understanding of the invention, reference is made to the following detailed description of several embodiments of the invention taken in conjunction with the figures of the accompanying drawing, in which.

DETAILED DESCRIPTION OF A PREFERRED EMBODIMENT

Figure 1:
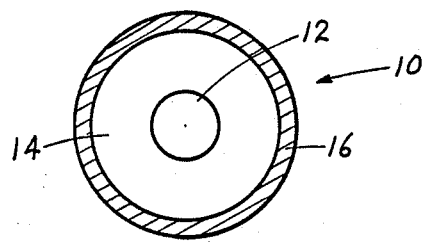
FIG. 1 is a cross-section of an optical fiber coated in accordance with this invention.

In FIG. 1, there is illustrated a solid optical fiber 10 of the type utilized in fiber optic systems to transmit voice, information or data signals in the form of light. The optical fiber 10 is generally conventional and includes a doped fused silica ($SiO_2$) core 12 and a doped or undoped fused silica cladding 14. As is conventional, the cladding 12 has a lower index of refraction than the core to enable the light to be transmitted through the fiber. Suitable dopants for the core include germania, phosphorous or any material raising the index of refraction of the silica; suitable dopants for the cladding include fluorine or any material that depresses the index of refraction of silica. Conventional fibers used in fiber optics have a small diameter, on the order of 100 to 150 microns.

Around the cladding 14 is a single coating 16 of a metal, metal alloy or dielectric material. No other coating is applied to the fiber so that the coating 16 is the only coating on it. The metal or dielectric is selected and applied such that it can withstand exposure to temperatures in excess of 300° C. without deterioration. In other words, the coating material must have a melting temperature in excess of 300° C. Examples of such metals are aluminum (Al), nickel (Ni), silicon (Si), titanium (Ti), copper (Cu), tungsten (W), and molybdenum (Mo); examples of such dielectrics are silicon nitride ($Si_3N_4$), tin oxide ($SnO_2$), boron nitride (BN), titanium oxide ($TiO_2$), aluminum oxide ($Al_2O_3$), silicon oxynitride (Si-O-N), silicon carbide (SiC) and boron carbide (BC). The coating must be applied in a way so as not to weaken the strength of the fiber and this is accomplished by the process described in my U.S. Pat. Nos. 4,518,628 and 4,575,463. Both of these patents, which are incorporated herein by reference, describe a process of coating a glass fiber with a metal, metal alloy or dielectric by means of a heterogeneous nucleation thermochemical deposition process (HNTD). This is a vapor phase reaction wherein the surface of the fiber is heated to a predetermined temperature and exposed to reactant gases so that a chemical reaction takes place on the hot surface of the fiber so that the coating material is deposited directly on it. One difference between the coated fiber according to this invention and the coated fiber described in my above-referenced patents is that the fiber in this invention does not include a second outer coating of polymeric material. A second difference is that the fiber of this invention is a high temperature resistant fiber.

As an example, a single mode optical fiber was coated with nickel (Ni) and another such fiber was coated with aluminum (Al) by the process described in the above-noted U.S. Pat. No. 4,575,463. The reactants were triisobutyl aluminum and isobutylene at 260° C. for the aluminum and nickel carbonyl at 200° C. for the nickel.

Figure 2:
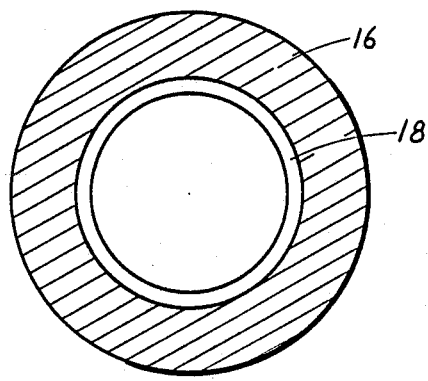
FIG. 2 is a cross-section of a capillary coated in accordance with this invention.

In FIG. 2, there is illustrated the use of the high temperature resistant coating 16 on a capillary tube 18. The capillary tube 18 is made of any suitable glass material and can be of any suitable inner and outer diameters, it being understood that the material and diameters are dependent on the intended use of the coated tube. The single coating 16 is deposited on the outer surface of the tube 18. These tubes are drawn down to their relatively small diameter from a large tube in much the same manner as the optical fiber 10 described above is drawn down from a larger solid preform. Thus, the deposition process for the capillary embodiment is the same as that described above and in my above-referenced patents which describe the HNTD process.

As examples, capillaries have been coated with aluminum, nickel and tin oxide in the same manner described for the optical fibers. In addition, capillaries have been coated with alloys such as iron (Fe), chrome (Cr), and cobalt (Co) in nickel (Ni).

While in the foregoing there have been described two embodiments of this invention, it should be understood by those skilled in the art that various modifications and changes can be made without departing from the true spirit and scope of this invention as recited in the appended claims.

I claim:

1. A combination, comprising a glass fiber having an outer surface and a single high temperature resistant coating on said outer surface for enabling said combination to be employed in environments having temperatures exceeding 300° C. without any additional coatings thereon, said single high temperature resistant coating being formed of a material having a melting temperature in excess of 300° C. selected from the group consisting of metal, metal alloy or a dielectric material, said high temperature resistant coating deposited on said surface by a heterogeneous nucleation thermochemical deposition process.

2. The combination recited in claim 1, wherein said material is selected from the group consisting of aluminum, nickel, silicon, titanium, copper, tungsten, molybdenum, tin oxide, silicon nitride, boron nitride, titanium oxide, aluminum oxide, silicon oxynitride, silicon carbide and boron carbide.

3. The combination recited in claim 1, wherein said melting temperature is in excess of 500° C.

4. The combination recited in claim 1, wherein said dielectric includes metal oxides, nitrides and carbides.

5. The combination recited in claim 1, wherein said coating has a fine grained structure without growth cones.

6. A combination, comprising a glass capillary having an outer surface and a single high temperature resistant coating on said outer surface for enabling said combination to be employed in environments having temperatures exceeding 300° C. without any additional coatings thereon, said single high temperature resistant coating being formed of a material having a melting temperature in excess of 300° C. selected from the group consisting of metal, metal alloy, or a dielectric material, said high temperature resistant coating deposited on said surface by a heterogeneous nucleation thermochemical deposition process.

7. The combination recited in claim 6, wherein said material is selected from the group consisting of aluminum, nickel, silicon, titanium, copper, tungsten, molybdenum, tin oxide, silicon nitride, boron nitride, titanium oxide, aluminum oxide, silicon oxynitride, silicon carbon and boron carbide.

8. The combination recited in claim 6, wherein said melting temperature is in excess of 500° C.

9. The combination recited in claim 6, wherein the dielectric includes metal oxides, nitrides and carbides.

10. The combination as recited in claim 6, wherein said coating has a fine grained structure without growth cones.

* * * * *